United States Patent [19]
Oe

[11] Patent Number: 5,392,211
[45] Date of Patent: Feb. 21, 1995

[54] IMAGE PROCESSING APPARATUS

[75] Inventor: Mitsuo Oe, Ootawara, Japan

[73] Assignee: Kabushiki Kaisha Toshiba, Kawasaki, Japan

[21] Appl. No.: 799,281

[22] Filed: Nov. 27, 1991

[30] Foreign Application Priority Data

Nov. 30, 1990 [JP] Japan .................. 2-340305

[51] Int. Cl.$^6$ ............................................. G06F 15/42
[52] U.S. Cl. ........................ 364/413.14; 364/413.13; 364/413.23; 382/54; 382/56; 382/41; 348/618; 348/619; 348/620
[58] Field of Search ............ 364/413.14, 413.13, 364/413.23; 382/56, 54, 41; 348/607, 618, 619, 620

[56] References Cited

U.S. PATENT DOCUMENTS

| | | | |
|---|---|---|---|
| 4,558,462 | 12/1985 | Horiba et al. | 382/42 |
| 4,635,293 | 1/1987 | Watanabe | 382/44 |
| 4,636,953 | 1/1987 | Kageyama | 364/414 |
| 4,644,582 | 2/1987 | Morishita et al. | 382/6 |
| 4,747,157 | 5/1988 | Kurakake et al. | 382/54 |
| 4,895,431 | 1/1990 | Tsujiuchi et al. | 350/320 |
| 4,899,393 | 2/1990 | Morishita et al. | 382/6 |
| 5,029,586 | 7/1991 | Honda | 364/413.23 |
| 5,090,038 | 2/1992 | Asahina | 378/41 |

FOREIGN PATENT DOCUMENTS 1-286579 11/1989 Japan .

Primary Examiner—Gail O. Hayes
Assistant Examiner—Gita D. Shingala
Attorney, Agent, or Firm—Finnegan, Henderson, Farabow, Garrett & Dunner

[57] ABSTRACT

A frame image signal which is output cyclically is converted to a digital signal and input to a first multiplier in a digital filter. The first multiplier multiplies a digital image signal $Y_i$ of each frame by (1-a), and supplies the product $(1-a)\cdot Y_i$ to a first input terminal of an adder. The coefficient a is a negative coefficient whose absolute value is not more than 1, so that (1-a) becomes a positive coefficient of not less than 1. An output of the adder serves as an output $Y_i'$ of the digital filter from which the residual image has been erased, and is supplied to a subsequent unit, e.g., a display unit (not shown) connected to the output of the adder. The output $Y_i'$ of the adder is also supplied to a frame memory and is delayed by one frame period. Therefore, an output $Y_{i-1}'$ of the frame memory is a one-frame preceding image output. The signal $Y_{i-1}'$ is input to a second multiplier and is multiplied by the coefficient a. The product is input to a second input terminal of the adder.

17 Claims, 4 Drawing Sheets

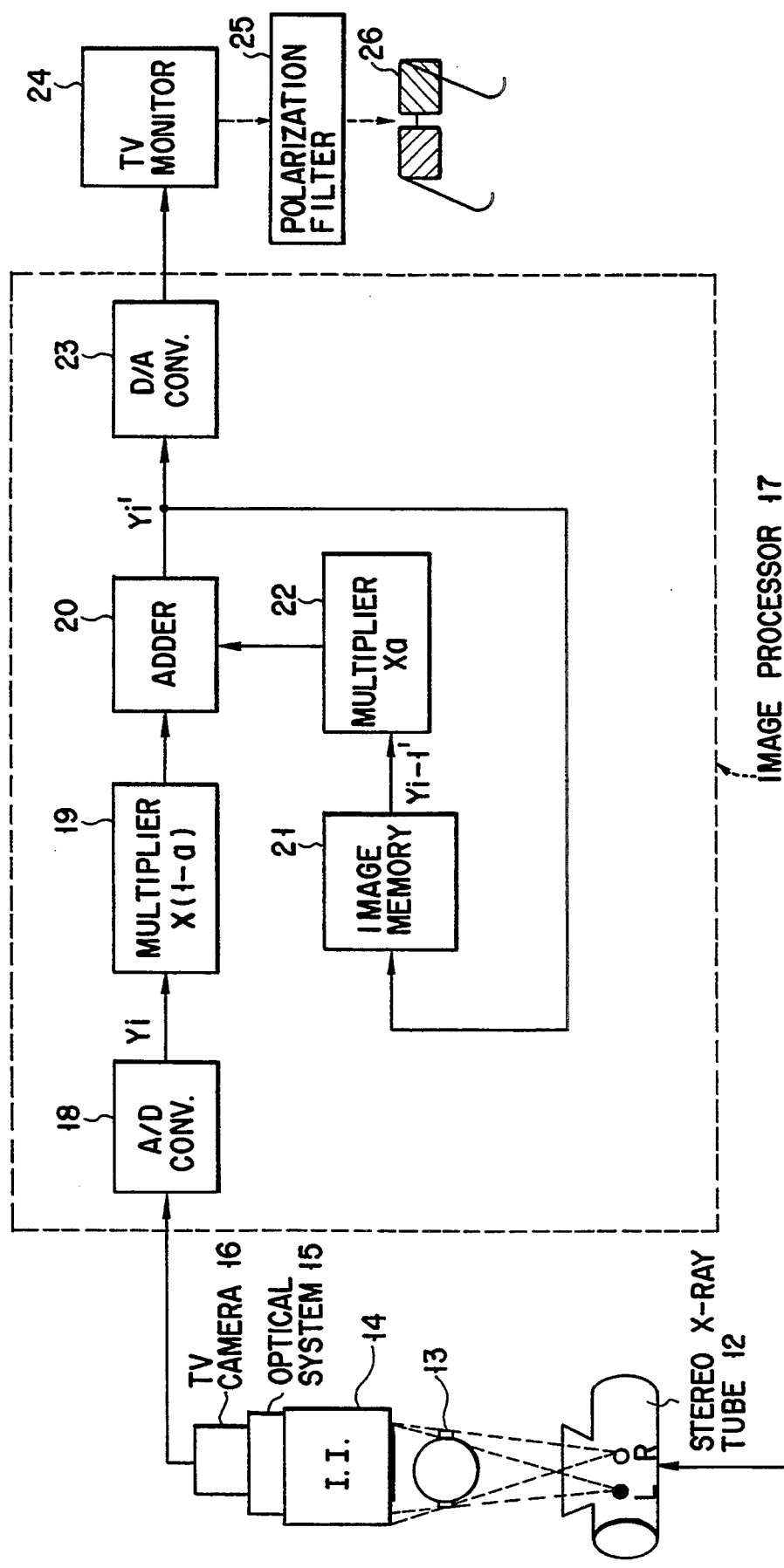
F I G. 2

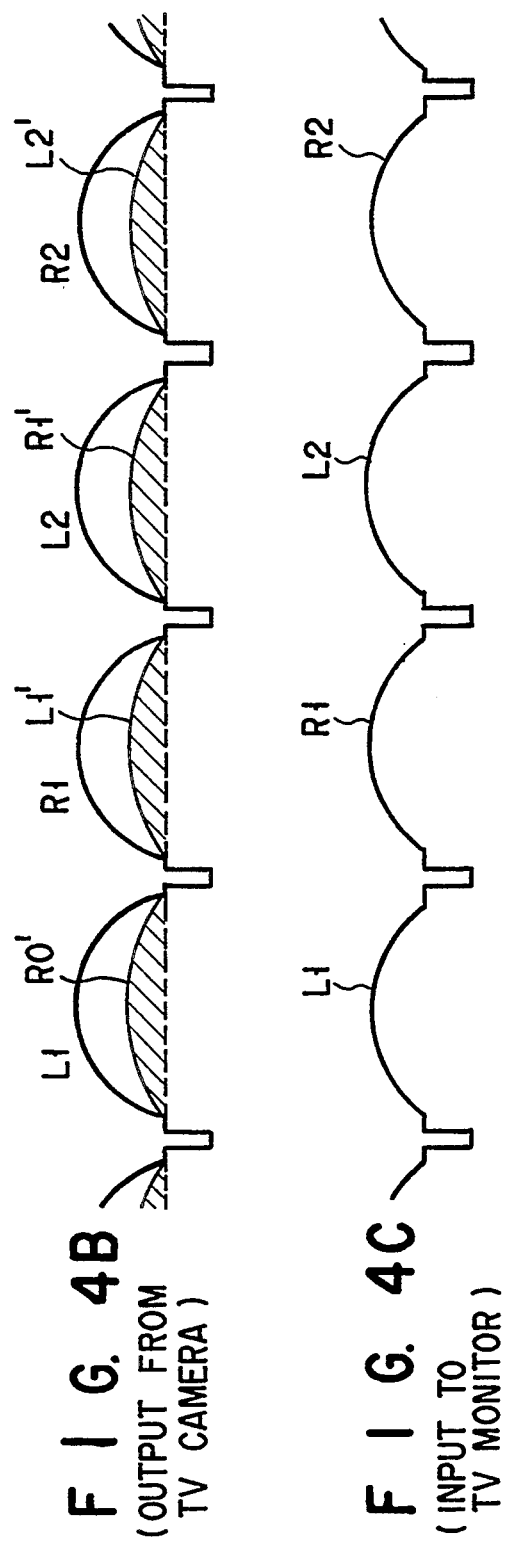
FIG. 4A (X-RAY PULSE)
FIG. 4B (OUTPUT FROM TV CAMERA)
FIG. 4C (INPUT TO TV MONITOR)

IMAGE PROCESSING APPARATUS

BACKGROUND OF THE INVENTION

1. Field of the Invention

The present invention relates to an image processing apparatus for erasing a persistence of vision, so-called a residual image, in an output image signal of a TV camera.

2. Description of the Related Art

Recently, along with an improvement in technology of a television (TV) camera and a TV monitor, imaging is performed in various fields. In the field of X-ray diagnosing apparatus, an X-ray TV system has been developed in which, in stead of obtaining an X-ray radiograph of an object to be examined using an X-ray film, the X-ray image is converted into an optical image by an image intensifier, a fluoroscopic optical image is then picked up by a TV camera, and the fluoroscopic image is displayed on a TV monitor. If a stereoscopic X-ray tube having right and left focal points is used as an X-ray tube to radiate X-rays alternately from its right and left focal points, and right and left fluoroscopic images are picked up and observed by right and left eyes respectively, a stereoscopic X-ray TV system which can obtain a stereoscopic fluoroscopic image of the object to be examined can be realized, which is much more useful in diagnosis than a conventional two-dimensional X-ray imaging system.

In such a stereoscopic X-ray TV system, the right and left fluoroscopic images formed by the X-rays radiated from the right and left focal points are detected by one image intensifier and one TV camera. The right and left images must be strictly separated and respectively observed by right and left eyes. However, in a general TV camera, an image signal preceding the current image signal by one field or frame remains in the image signal of the current field or frame because of the residual image characteristic of the image pickup surface. Therefore, the right and left fluoroscopic images cannot be separately observed strictly by the right and left eyes. The right and left fluoroscopic images are mixed and displayed on a display screen, thereby the image cannot be observed stereoscopically. About 10% residual image normally remains in the image pickup surface of the TV camera.

The above description is given with reference to the stereoscopic X-ray TV system. However, an influence of the residual image is similarly found in a general imaging system using a TV camera.

SUMMARY OF THE INVENTION

Accordingly, it is an object of the present invention to provide an image processing apparatus which erases, with a simple construction, a residual image of an image signal of a previous frame.

According to one aspect of the present invention, there is provided an image processing apparatus to which image signals are periodically input, the apparatus comprising means for storing the processed image signal which is preceding the input image signal by one cycle, and arithmetic means for subtracting the input image signal from the processed image signal stored in the storing means at least one of which image signals being multiplied by a coefficient.

In the image processing apparatus according to the present invention, an image signal from which a residual image is erased can be obtained in a real time manner in units of cycles by setting the coefficient to a negative value in accordance with a residual image coefficient of the image signal.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 is a block diagram showing a construction of a stereoscopic X-ray fluoroscopic apparatus according to a second embodiment of the present invention;

FIGS. 4A to 4C are a signal waveform diagram showing the operation of the second embodiment.

DETAILED DESCRIPTION OF THE PREFERRED EMBODIMENTS

Figure 1:
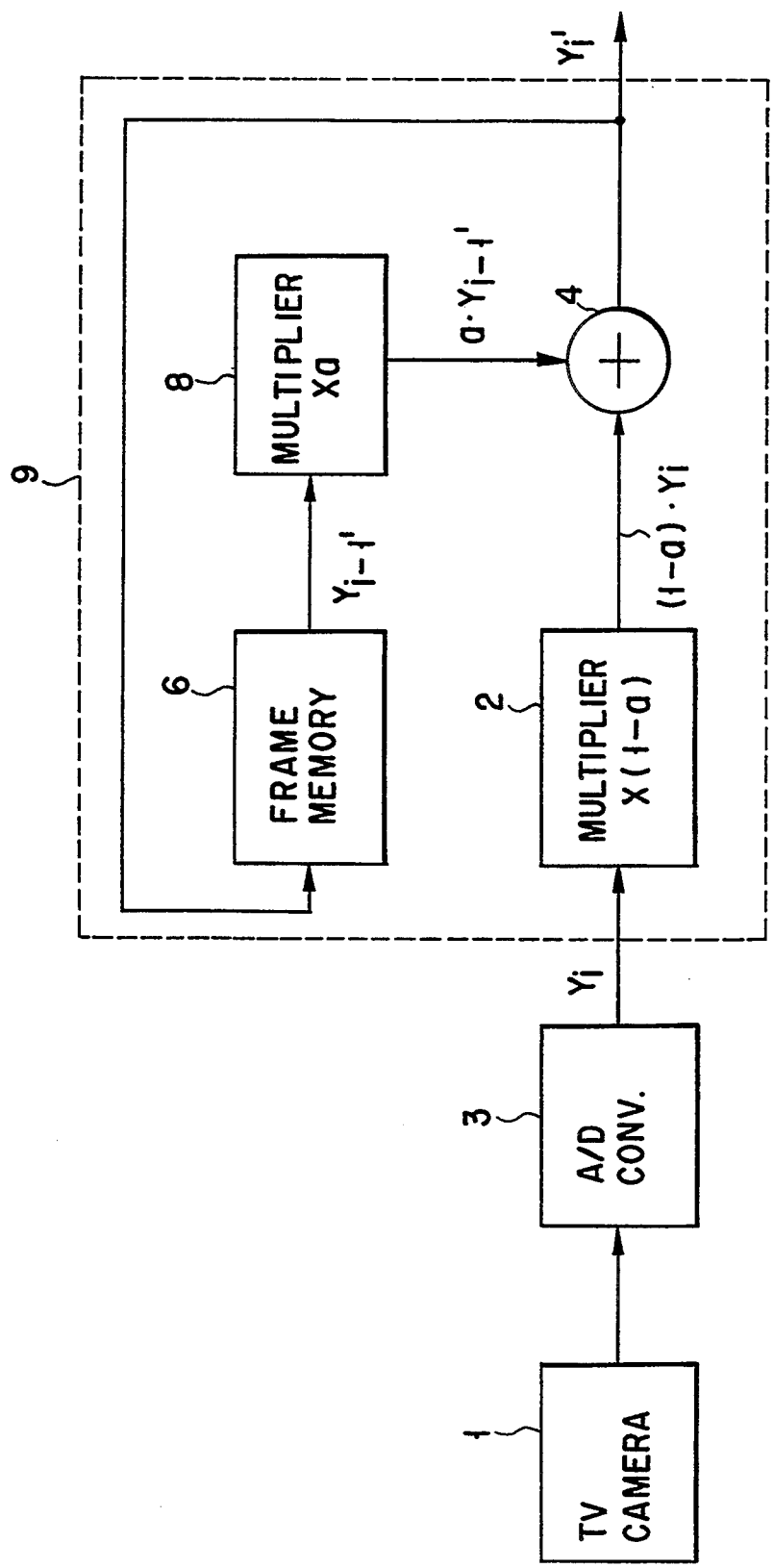
FIG. 1 is a block diagram showing a construction of an image processing apparatus according to a first embodiment of the present invention.

A preferred embodiment of an image processing apparatus according to the present invention will now be described with reference to the accompanying drawings. FIG. 1 is a block diagram showing the construction of the first embodiment of the present invention. The image processing apparatus according to the first embodiment comprises a recursive digital filter 9 in which an image signal cyclically generated is input, an input image signal of each cycle and a processed output signal of a previous cycle are added together after being multiplied by corresponding coefficients to produce a processed output signal of the current cycle. This recursive digital filter 9 differs from the conventional digital filter in that the coefficient to be multiplied to the signal of the previous cycle is negative. An output signal from a TV camera 1 is input to a multiplier 2 through an A/D converter 3. Though a conventional TV camera 1 picks up sixty field images, i.e., thirty frame images per minute in an interlace manner, the TV camera 1 produces thirty frames per minute in a non-interlace manner for the sake of simplicity of the description. The multiplier 2 multiplies the digital image signal $Y_i$ (i denotes the number of the frame) of each frame by a coefficient $(1-a)$. The product $(1-a)\cdot Y_i$ is supplied to a first input terminal of an adder 4. An arbitrary constant a is a negative constant satisfying a condition of $0 > a > -1$, therefore, the coefficient $(1-a)$ becomes a positive constant of 1 or more. An output from the adder 4 serves as an output $Y_i'$ of the digital filter 9 from which the residual image has been erased and is supplied to a subsequent unit, e.g., a display unit (not shown).

The output $Y_i'$ of the adder 4 is also supplied to a frame memory 6. The frame memory 6 delays a signal by one frame period, i.e., 1/30 second, and outputs the delayed signal. That is, an output $Y_{i-1}'$ of the frame memory 6 corresponds to the output of the digital filter 9 which precedes the input signal to the digital filter 9 by one frame. This output signal $Y_{i-1}'$ is input to a multiplier 8. The multiplier 8 multiplies the one-frame preceding image signal $Y_{i-1}'$ by a coefficient a and outputs the product $a \cdot Y_{i-1}'$ to a second input terminal of the adder 4. As described above, the coefficient a of the multiplier 8 is a negative constant whose absolute value is 1 or less.

The operation of the first embodiment having the above construction will be described. The image signal (an input signal to the digital filter 9) $Y_i$ of each frame of the TV camera 1 does not strictly correspond to the input image information of the current frame to the camera 1 because of its residual image characteristic. The output frame signal $Y_i$ of the TV camera 1 can be expressed as follows:

$$Y_i = X_i + k \cdot Y_{i-1} \quad (1)$$

where $X_i$ is input image information of the current frame to the camera, $Y_{i-1}$ is a one-frame preceding output from the camera 1, and k (a positive decimal not more than 1 which indicates the degree of residual image, included in the camera output of the current frame, of the camera output of the immediately preceding frame) is a residual image coefficient. It should be noted that the coefficient k is not constant for the entire frame but is determined for every pixel. However, in this embodiment, the coefficient k denotes an average of the coefficients of all the pixels in one frame.

From the circuit construction of FIG. 1, the output $Y_i'$ of the digital filter 9 can be expressed as:

$$Y_i' = (1-a) \cdot Y_i + a \cdot Y_{i-1}' \quad (2)$$

Substitution of equation (1) into equation (2) yields:

$$\begin{aligned} Y_i' &= (1-a) \cdot (X_i + k \cdot Y_{i-1}) + a \cdot \\ &\quad \{(1-a) \cdot Y_{i-1} + a \cdot Y_{i-2}\} \\ &= (1-a) \cdot X_i + (1-a) \cdot (k+a) \cdot \\ &\quad Y_{i-1} + a^2 \cdot Y_{i-2} \end{aligned} \quad (3)$$

If $a = -k$, the second term of the right-hand side of equation (3) becomes 0. Since k is usually about 10% (=0.1), $a^2$ (=0.01)=0. Therefore, the third term also becomes 0, and as a result the output $Y_i'$ of the digital filter 9 can be expressed as:

$$Y_i' = (1-a) \cdot X_i \quad (4)$$

From equation (4), it is apparent that even if the image signal of each frame output from the TV camera 1 includes the residual image of the preceding frame about 10%, the residual image component $Y_{i-1}$ can be erased from the image signal $Y_i'$ of each frame output from the digital filter by setting $a = -k$.

In this manner, according to the first embodiment, in the digital filter 9 which processes an output frame signal of the TV camera 1, the residual image can be erased from the output of the TV camera 1 with a simple construction by setting the coefficient of the multiplier 8 which processes a one-frame preceding filter output to a negative value in accordance with the residual image coefficient. Also, since the digital filter 9 obtains an output signal by adding a signal, from which the one-frame preceding residual image has been erased, to the input signal of each frame, a signal from which the residual image has been erased can be output in units of frames in a real time manner.

A stereoscopic X-ray fluoroscopic apparatus as the second embodiment will be described with reference to FIG. 2. A stereoscopic X-ray tube 12 and an image intensifier 14 are arranged to oppose each other intervening an object 13 to be examined therebetween. The stereoscopic X-ray tube 12 has right and left focal points R and L spaced apart from each other by a predetermined distance (normally 35 to 65 mm) and radiates pulsed X-rays onto the object 13 alternately from its right and left focal points R and L upon reception of high-voltage pulses from a high voltage generator 11. The X-ray image transmitted through the object 13 is converted to an optical image by the image intensifier 14 and incident on a TV camera 16 through an optical system 15 integrally formed with the image intensifier 14. Thus, an X-ray fluoroscopic image is picked up by the TV camera 16. The TV camera 16 employs the non-interlace scheme and cyclically outputs an image signal corresponding to one frame.

An output from the TV camera 16 is input to an image processor 17 according to the present invention which has a recursive digital filter for residual image erasure. The image signal of each frame is first input to a multiplier 19 via an A/D converter 18. The multiplier 19 multiplies an image signal $Y_i$ of each frame by a coefficient $(1-a)$ and supplies the product to a first input terminal of an adder 20. It is noted that $a = -k$ where k is a residual image coefficient of the TV camera 16 and is usually a positive decimal not more than 1. Therefore, when a residual image is present about 10%, $a = -0.1$. The output $Y_i'$ from the adder 20 is supplied to a TV monitor 24 via a D/A converter 23 as an output from the image processing apparatus 17 from which the residual image has been erased.

The output $Y_i'$ from the adder 20 is also supplied to an image memory 21. The image memory 21 has a memory capacity capable of storing signals corresponding to one frame, delays a signal by one frame period, and outputs a delayed signal. Therefore, an output $Y_{i-1}'$ of the adder 20 which precedes, by one frame, the output signal $Y_i'$ of the TV camera 16 of each frame which is to be processed by the multiplier 19 is processed by a multiplier 22. The multiplier 22 multiplies the input signal $Y_{i-1}'$ by a and supplies the product to a second input terminal of the adder 20. Therefore, the adder 20 outputs $Y_i' = (1-a) \cdot Y_i + a \cdot Y_{i-1}'$. From equations (2) to (4), it is apparent that the residual image component $Y_{i-1}$ can be erased from the image signal $Y_i'$ of each frame by setting $a = -k$.

The TV monitor 24 alternately displays the right and left fluoroscopic images obtained by alternatively radiating the pulsed X-rays from the right and left focal points R and L of the stereoscopic X-ray tube 12. For the purpose of stereoscopic vision, a polarization filter 25 is provided in front of the screen of the TV monitor 24. The plane of polarization of the polarization filter 25 changes in an interlocked manner with the alternate display of the right and left fluoroscopic images, and the polarization filter 25 polarizes the right and left fluoroscopic images such that their planes of polarization are perpendicular to each other. The observer observes the display image of the TV monitor 24 with polarization glasses 26. The polarization glasses 26 have right and left filters of the same planes of polarization as those of the right and left polarized fluoroscopic images, so that the right and left polarized fluoroscopic images can be observed by the observer with only the right and left eyes.

Figure 3B:
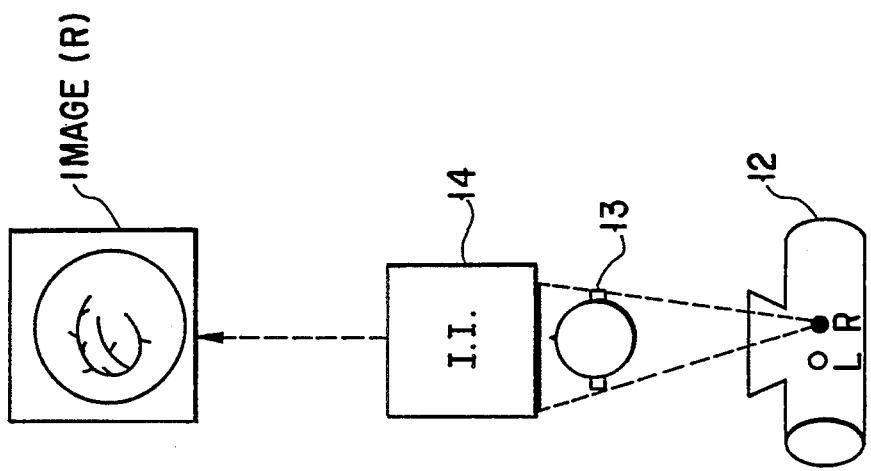
FIGS. 3A and 3B are views showing the principle of stereoscopic fluoroscopy of the second embodiment.
Figure 3A:
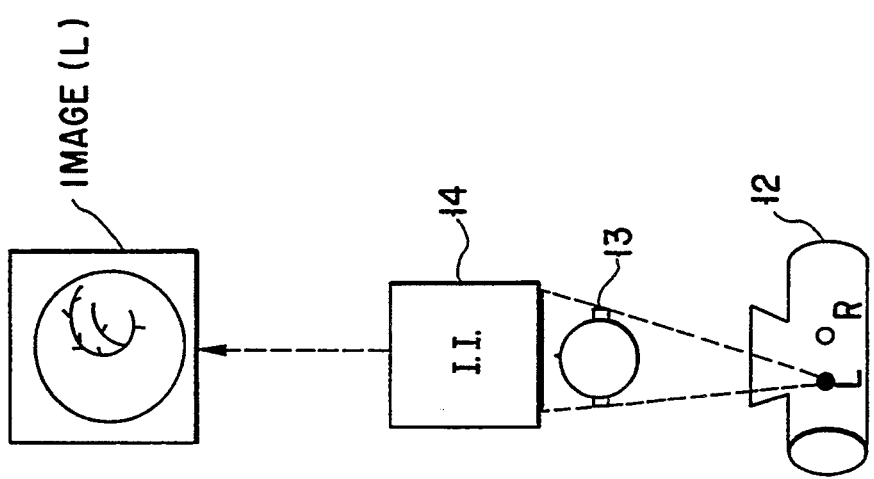

The operation of the second embodiment will be described. The high voltage generator 11 causes the X-ray tube 12 to radiate pulsed X-rays L1, R1, . . . to the object 13 alternately from the right and left focal points R and L at a predetermined interval, as shown in FIG. 4A. Since the right and left focal points R and L are spaced apart from each other by a predetermined distance, L and R fluoroscopic images obtained by the X-rays radiated by the focal points R and L have different projection angles, as shown in FIGS. 3A and 3B, and a predetermined parallax occurs between them. Therefore, the object 13 can be seen in a stereoscopic manner by separating the R and L fluoroscopic images between the right and left eyes and observing them separately.

The pulsed X-ray radiation timing and the operation cycle of the TV camera 16 are synchronized with each other. A pulsed X-ray is radiated in synchronism with a frame sync. pulse of the TV camera 16. Therefore, when a pulsed X-ray is radiated from the right focal point R, a right fluoroscopic image is output from the TV camera 16, and when a pulsed X-ray is radiated from the left focal point L, a left fluoroscopic image is output from the TV camera 16, as indicated by solid lines in FIG. 4B. It is noted that since the TV camera 16 has a residual image characteristic, the right and left fluoroscopic image signals $R_i$ and $L_i$ include about 10% left and right fluoroscopic image components $L_{i-1}'$ and $R_{i-1}'$, respectively, of the preceding frame, as indicated by hatched portions in FIG. 4B. When an output from the TV camera 16 is supplied to the image processing apparatus 17, the residual image (a one-frame preceding image signal) is erased, as described above, and only the right and left fluoroscopic images $R_i$ and $L_i$ are alternately output from the image processing apparatus 17 in an interlocked manner with alternate pulsed X-ray radiation, as shown in FIG. 4C, and are alternately displayed by the TV monitor 24.

Therefore, according to the second embodiment, mixed display of the right and left fluoroscopic images on the display screen which leads to unclear stereoscopic vision or which makes stereoscopic vision impossible can be prevented in the stereoscopic X-ray apparatus. It is preferable that the coefficient a of the multiplier 22 is variable according to the residual image characteristic of the TV camera 16 or is automatically changed according to the luminance level of each pixel in the image signal.

As has been described above, according to the present invention, there is provided an image processing apparatus which erases a residual image from an output image signal of a TV camera with a simple hardware construction and in a real time manner by utilizing a recursive digital filter.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

For example, in the above description, the TV camera is of the non-interlace scheme and outputs image signals of one frame in units of cycles. However, the present invention can similarly be applied when image signals in units of fields are to be cyclically output with the interlace scheme. In this case, the camera output of each field and a one-field preceding processor output may be added to each other after being multiplied by $(1-a)$ and a, respectively. In the second embodiment, the right and left fluoroscopic images are alternately displayed in one screen. However, the stereoscopic display method is not limited to this. Any other methods, e.g., a method of displaying right and left fluoroscopic images on two screens in a parallel manner using an optical system for respectively guiding the right and left images to the right and left eyes, may be employed. Further, it is possible to use a conventional X-ray tube having a single focal point instead of the stereoscopic X-ray tube for a stereoscopic fluoroscopy, as described in the U.S. patent application Ser. No. 07/592,375 (filed on Oct. 3, 1990 and allowed on Sep. 6, 1991). In this case, two X-ray pluses are radiated from different angles with changing the radiating direction of the X-ray tube. The present invention is not limited to a stereoscopic X-ray apparatus but can be similarly applied to a simple imaging apparatus which does not perform stereoscopic vision. It is to be noted that in the case of the X-ray apparatus, it can be applied not only to a simple fluoroscopic apparatus but also to an angiography apparatus which performs subtraction of images before and after injection of a contrast medium into a blood vessel. Though both of the input signal and the processed signal are multiplied by the respective coefficients $(1-a)$ and a, it is possible to change these coefficients with keeping the ratio therebetween. For example, they can be changed to $(1-a)/a$ and 1 or 1 and $a/(1-a)$. Therefore, it is sufficient to multiply at least one of the input signal and the processes signal by a coefficient which is determined by a ratio of $(1-a)$ to a.

What is claimed is:

1. An image processing apparatus for removing a residual image in an output image signal, receiving an image signal cyclically output from a TV camera, processing the image signal received, and outputting a processed image signal, the apparatus comprising:

means for storing a processed image signal $Y_i$ where i is an integer and $Y_i$ corresponds to an image number which precedes an image signal $Y_{i+1}$ output from the TV camera by one cycle;

means for removing a residual image by multiplying the image signal $Y_{i+1}$ output from the TV camera by a first coefficient and the processed image signal $Y_i$ stored in said storing means by a second coefficient and adding the results of the two multiplications together; and means for displaying an output of said removing means.

2. An apparatus according to claim 1, wherein the first coefficient is $(1-a)$ where a is an arbitrary constant satisfying $0 > a > -1$ and the second coefficient is a.

3. An apparatus according to claim 2, wherein said removing means comprises:

first means for multiplying the image signal cyclically output from the TV camera by the first coefficient $(1-a)$;

second means for cyclically multiplying the processed image signal stored in said storing means by the second coefficient a; and means for adding products output from said first and second means together.

4. An apparatus according to claim 2, wherein said TV camera outputs an image signal $Y_i$ of each cycle i as follows:

$$Y_i = X_i + k \cdot Y_{i-1}$$

where $X_i$ is input image information of the current cycle to the TV camera, $Y_{i-1}$ is a one-cycle preceding output from the TV camera, and k (a positive decimal not more than 1 which indicates the degree of residual image, included in the TV camera output of the current cycle, of the TV camera output of the immediately preceding cycle) is a residual image coefficient.

5. An X-ray image displaying apparatus, comprising:
X-ray image detection means for radiating an X-ray to an object and receiving an X-ray image transmitted through the object to output an optical image of the X-ray image;
image pick-up means for picking up the optical image output from said X-ray image detection means and for cyclically outputting an image signal corresponding to the optical image;
image processing means for receiving the image signal output from said image pick-up means, multiplying the image signal of each cycle output from the image pick-up means by a first coefficient and a processed image signal preceding to the image signal output from said image pick-up means by one cycle by a second coefficient, and adding the results of said multiplication together; and
means for displaying an output of said image processing means.

6. An apparatus according to claim 5, wherein the first coefficient is $(1-a)$ where a is an arbitrary constant satisfying $0 > a > -1$ and the second coefficient is a.

7. An apparatus according to claim 6, wherein said image processing means comprises:
first means for multiplying the image signal cyclically output from said image pick-up means by the first coefficient $(1-a)$;
second means for cyclically multiplying the processed image signal preceding to the image signal output from said image pickup means by one cycle by the second coefficient a; and
means for adding products output from said first and second means together.

8. An apparatus according to claim 6, wherein said image pick-up means outputs an image signal $Y_i$ of each cycle i as follows:

$$Y_i = X_i + k \cdot Y_{i-1}$$

where $X_i$ is input image information of the current cycle to the image pick-up means, $Y_{i-1}$ is a one-cycle preceding output from the image pick-up means, and k (a positive decimal not more than 1 which indicates the degree of residual image, included in the image signal of the current cycle, of the image signal of the immediately preceding cycle) is a residual image coefficient.

9. An X-ray image displaying apparatus, comprising:
means for radiating X-rays to an object in a plurality of directions;
means for detecting X-ray images transmitted through the object in the plurality of directions to output optical images of the X-ray images;
image pick-up means for picking up the optical images output from said detecting means and for cyclically outputting image signals corresponding to the optical images;
image processing means for receiving the image signals output from said image pick-up means, multiplying the image signal of each cycle output from the image pick-up means by a first coefficient and a processed image signal preceding the image signal output from said image pick-up means by one cycle by a second coefficient and adding the results of said multiplication together; and
means for stereoscopically displaying an output of said image processing means.

10. An apparatus according to claim 9, wherein said image processing means multiplies the image signal output from said image pick-up means by the first coefficient $(1-a)$ (where a is an arbitrary constant satisfying $0 > a > -1$) and the processed image signal preceding to the image signal output from said image pick-up means by one cycle by the second coefficient a.

11. An apparatus according to claim 10, wherein said image processing means comprises:
first means for multiplying the image signal cyclically output from said image pick-up means by the first coefficient $(1-a)$;
second means for cyclically multiplying the processed image signal preceding to the image signal output from said image pick-up means by one cycle by the second coefficient a; and
means for adding products output from said first and second means together.

12. An apparatus according to claim 10, wherein said image pick-up means outputs an image signal $Y_i$ of each cycle i as follows:

$$Y_i = X_i + k \cdot Y_{i-1}$$

where $X_i$ is input image information of the current cycle to the image pick-up means, $Y_{i-1}$ is a one-cycle preceding output from the image pick-up means, and k (a positive decimal not more than 1 which indicates the degree of residual image, included in the image signal of the current cycle, of the image signal of the immediately preceding cycle) is a residual image coefficient.

13. An apparatus according to claim 9, wherein said radiating means comprises a stereoscopic X-ray tube having right and left focal points and radiating pulsed X-rays onto the object alternately from the right and left focal points; and
said displaying means comprises means for alternately displaying right and left images and optical means for guiding the right and left images respectively to right and left eyes using a shutter which is on/off in synchronism with an alternate display of the right and left images.

14. An apparatus according to claim 9, wherein said radiating means comprises a stereoscopic X-ray tube having right and left focal points and radiating pulsed X-rays onto the object alternately from the right and left focal points; and
said displaying means comprises means for simultaneously displaying right and left images and optical means for guiding the right and left images respectively to right and left eyes.

15. A recursive digital filter for processing an image signal to remove a residual image in an output image signal, comprising:

means for storing output signal from the digital filter for a period of time corresponding to one frame of the image signal;

first means for multiplying the image signal input to the digital filter by a first coefficient $(1-a)$ where a is an arbitrary constant satisfying $0 > a > -1$;

second means for multiplying the output signal stored in said storing means by a second coefficient a; and means for outputting a sum of products from said first and second means as a processed image signal.

16. An image processing apparatus for removing a residual image in an output image signal, receiving an image signal cyclically output from a TV camera, processing the image signal received, and for outputting a processed image signal, the apparatus comprising:

means for storing the processed image signal $Y_i$ where i is an integer and $Y_i$ corresponds to an image number which precedes an image signal $Y_{i+1}$ output from the TV camera by one cycle;

means for removing a residual image by subtracting the image signal $Y_{i+1}$ output from the TV camera from the processed image signal $Y_i$ stored in said storing means with at least one of the image signals being multiplied by a coefficient; and means for displaying an output of said removing means.

17. An apparatus according to claim 16, wherein said removing means comprises:

means for multiplying the image signal output from the TV camera and the processed image signal stored in said storing means by first and second coefficients, a ratio of the first coefficient to the second coefficient being $(1-a)$ to a where a is an arbitrary constant satisfying $0 > a > -1$; and means for adding both products obtained by said multiplying means.

* * * * *